United States Patent [19]
Tao et al.

[11] Patent Number: 5,713,369
[45] Date of Patent: Feb. 3, 1998

[54] UTERINE ENDOMETRIAL TISSUE SAMPLE BRUSH

[75] Inventors: Liang-Che Tao, Carmel, Ind.; John A. Maksem, Waukee, Iowa

[73] Assignee: Vance Products Inc., Spencer, Ind.

[21] Appl. No.: 527,838

[22] Filed: Sep. 13, 1995

[51] Int. Cl.⁶ ............................................. A61B 10/00
[52] U.S. Cl. ............................................. 128/756
[58] Field of Search ........................... 128/748, 756, 128/757, 759

[56] References Cited

U.S. PATENT DOCUMENTS

| | | | |
|---|---|---|---|
| D. 317,361 | 6/1991 | Stormby | D24/141 |
| 2,701,559 | 2/1955 | Cooper. | |
| 3,881,464 | 5/1975 | Levene. | |
| 4,227,537 | 10/1980 | Suciu et al. | 128/756 |
| 4,235,244 | 11/1980 | Abele et al. | 128/749 |
| 4,754,764 | 7/1988 | Bayne | 128/756 |
| 4,759,376 | 7/1988 | Stormby | 128/756 |
| 4,763,670 | 8/1988 | Manzo | 128/756 |
| 4,966,162 | 10/1990 | Wang | 128/750 |
| 5,133,361 | 7/1992 | Cox et al. | 128/757 |
| 5,146,928 | 9/1992 | Esser | 128/756 |
| 5,184,626 | 2/1993 | Hicken | 128/756 |
| 5,201,323 | 4/1993 | Vermeulen | 128/756 |
| 5,217,023 | 6/1993 | Langdon | 128/756 |
| 5,253,652 | 10/1993 | Fast | 128/756 |
| 5,370,128 | 12/1994 | Wainwright | 128/756 |
| 5,456,265 | 10/1995 | Yim | 128/756 |

FOREIGN PATENT DOCUMENTS

2159420  12/1985  United Kingdom.
9116855  11/1991  WIPO.

*Primary Examiner*—Max Hindenburg
*Attorney, Agent, or Firm*—Richard J. Godlewski

[57] ABSTRACT

A uterine endometrial tissue sample brush 10 includes a flexible core 12 having a distal core end 16 and a cylindrical brush member 18 carried adjacent the distal core end 16. The core 12 is formed from a spirally wrapped pair of wires 22 and includes an atraumatic tip 26. The brush member 18 is about 3 to 5 cm long and has a free outside diameter, preferably about 5.08 to 7.62 mm (0.2 to 0.3 in.), suited to maintain patient comfort yet comprehensively contact the undilated uterine canal 38. The brush member 18 includes a plurality of resilient bristles 20 axially spaced about 0.5 to 1.5 mm apart. The bristles 20 have a stiffness equivalent to that possessed by nylon-6,12 at a diameter of about 0.076 to 0.152 mm (0.003 to 0.006 in.). This stiffness is critical and unexpectedly gives the brush 10 good exfoliating and collecting abilities simultaneously, in contrast to prior devices which may possess either good exfoliating or good collecting abilities, but not both abilities at the same time. The bristles 20 are preferably composed of nylon-6,12 of about 0.127 mm (0.005 in.) diameter, and are retained between the pair of wires 22 so that they are spirally arrayed. The brush 10 also preferably includes a flexible sheath 24 adapted to slidably receive the core 12 and brush member 18 therein, to prevent the collection of undesired exocervical or vaginal fluid or material during introduction or removal of the brush 10. The brush 10 especially useful for routinely and repeatedly collecting samples for cancer screening or for monitoring ongoing estrogen replacement therapy.

27 Claims, 4 Drawing Sheets

UTERINE ENDOMETRIAL TISSUE SAMPLE BRUSH

TECHNICAL FIELD

This invention relates generally to medical devices, but more particularly to devices for obtaining samples of tissue from the uterine endometrium.

BACKGROUND OF THE INVENTION

It has become axiomatic that the best time to treat diseases such as cancer is when they are in their earliest phases. By necessity, the early treatment of such diseases requires that they be detected early. A variety of known techniques for detecting such diseases entail the scraping or sampling of tissue from the uterine or endocervical canal. Tissues so obtained can be subjected to cytopathic or other examinations, perhaps the most common method of examination being the Pap (Papanicolaou) smear.

The known devices for uterine endometrial tissue exfoliation and collection vary widely in complexity and utility. The most simple is a cotton swab introduced into the uterine canal. Wet spatulas have also been used to sample the exocervix and the uterine canal. Tissue samples have been aspirated through plastic or glass pipettes. Full dilation and curettage of the uterine canal has been employed, as have microcurettes. More recently, certain brushes have been especially adapted to either the exfoliation or the collection of endometrial tissue, but generally these brushes have not been adapted to perform both functions, let alone perform them well. The bristles of such brushes have in practice been designed to enhance the performance of one function at the expense of the other. That is, when their bristles are of a suitable length or stiff enough to exfoliate tissue well, they collect the exfoliated tissue poorly; and when the bristles are of a suitable length or flexible enough to collect tissue well, they fail to exfoliate sufficient tissue, or a sufficiently uniform sample of tissue.

These and other conventional devices and techniques for sampling uterine endometrial tissue have suffered numerous other drawbacks. Some sampling instrument diameters are uncomfortably large when inserted into the uterine canal, and their use can be sufficiently painful to the patient to require a general anesthetic. Some devices have undesirably low rates of successful insertion, while the use of others leads to unacceptably high rates of complications. Some devices have relatively poor yields (that is, inadequate sample sizes) when compared to conventional dilation and curettage. Full dilation and curettage, of course, entails its own trauma and disadvantages, including the infliction of open wounds requiring further post-procedural treatment. Moreover, early pathologic lesions generally tend to be small and show only local changes, so that sampling of only part of the endometrial cavity may miss significant abnormalities. Many devices fail to sample enough of the uterine canal to ensure that small, localized abnormalities are detected.

It is Applicants' belief that the known sampling devices are not capable of consistently meeting these requirements, and interfere with their use for regular and repeated screening of patients. It is therefore clear that it would be highly desirable to obtain a uterine endometrial tissue sample brush which simultaneously possessed both good ability to exfoliate uterine endometrial material and good ability to collect the exfoliated material, without having to trade one ability for the other. It would also be highly desirable for such a brush to be non-invasive and atraumatic, and be useful for annual or even more frequent screening, without scarring the endometrium and thereby interfere with the subsequent practice of other evaluative techniques. It would be further advantageous to find such a brush which was useful in the evaluation of a variety of conditions in a range of patients, particularly in patients at high risk for disease, and patients who have difficulty tolerating conventional endometrial sampling devices. It would also be advantageous to discover a brush which collected uterine endometrial tissue comprehensively from the uterine canal, ensuring that areas of the endometrium are not missed during sampling. Finally, it would be advantageous for such a brush to affirmatively prevent contamination of the exfoliated sample by endocervical and vaginal fluids and materials, thereby avoiding a significant source of diagnostic error. Normal endocervical cells may be mistaken during a Papanicolaou smear for endometrial cells in the secretory phase, and metaplastic squamous cells of the cervical epithelium may be mistaken for squamous metaplasia of the endometrium, or as a component of adenocarcinoma (adenocanthoma).

SUMMARY OF THE INVENTION

The foregoing problems are solved and a technical advance is achieved in an illustrative uterine endometrial tissue sample brush which simultaneously possesses good ability to exfoliate endometrial tissue without trauma to the uterine canal, and good ability to collect the exfoliated endometrial tissue. "Exfoliate" is used broadly herein, and is intended to include both tissue excision by sharp edges and tissue removal by surface rubbing or abrasion, in addition to other ways in which tissues can be separated for collection. The brush is most useful for the early detection of endometrial carcinoma and its precursors, and includes a brush member carried adjacent the distal end of a flexible brush core. Applicants have discovered that the good exfoliating and collecting abilities can be simultaneously achieved by employing a brush member having a free outside diameter suited to maintain patient comfort yet comprehensively contact the undilated uterine canal, preferably about 5.08 to 7.62 mm (0.2 to 0.3 in.), and more preferably about 5.97 mm (0.235 in.); the brush member including a plurality of resilient bristles axially spaced about 0.5 to 1.5 mm apart; and the bristles having a stiffness equivalent to that possessed by nylon-6,12 at a diameter of about 0.076 to 0.152 mm (0.003 to 0.006 in.). Such a stiffness unexpectedly gives the brush its good exfoliating and collecting abilities simultaneously, in contrast to prior endometrial sampling devices which may exhibit either good exfoliating or good collecting abilities, but not both at the same time.

The flexible core is preferably formed from a spirally wrapped pair of wires and includes an atraumatic tip at the distal core end. The brush member is preferably about 3 to 5 cm long. The bristles are preferably composed of nylon-6,12 of about 0.127 mm (0.005 in.) diameter and can be retained between the pair of wires so that they are spirally arrayed. In such a case, the individual turns of the spiral array so formed provide the axial spacing to the bristles, and give the brush the appearance (from a side view) of having discreet rows of bristles, even though these "rows" are in fact a single, continuous arrangement of bristles.

Of course, instead of being disposed in a continuous spiral array, the bristles can be arranged in discreet, axially spaced rows. Moreover, whether the arrangement is continuous or discreet, alternating or plural rows of the axially spaced bristles can have differing stiffnesses. Any convenient number of bristle rows having differing stiffnesses can be provided. While the average of the differing stiffnesses preferably falls in the range identified above, this is not essential to the practice of the present invention; some bristles can have stiffnesses outside the identified range, such as by having a smaller diameter, for example, about 0.0508 mm (0.002 in). Thus, each of the differing stiffnesses preferably but not necessarily falls within the range identified above.

The differing stiffnesses can be achieved in several ways, for example, by giving the axially spaced bristles differing diameters, compositions or lengths. The differing lengths can be provided in the continuous array of bristles retained between the spirally wrapped wires, by offsetting the centers of the individual bristles from the axis of the flexible core. Alternatively, the differing stiffnesses can be achieved by using differing stiffnesses for alternating bristles or alternating groups of bristles retained between the spirally wrapped wires. A particularly preferred alternative embodiment of the present invention comprises an arrangement of four 0.0025 in. (0.064 mm) diameter second bristles positioned between a series of 0.005 in. (0.127 mm) diameter first bristles, all of the bristles being of the same length. Other convenient groupings of bristles of different diameters, lengths or compositions, yielding different stiffnesses, fall within the scope of the present invention as well.

The uterine endometrial tissue sample brush of the present invention also preferably includes a flexible sheath adapted to slidably receive the core and brush member therein, and compressively contain the brush member therein, to prevent the collection of undesired exocervical or vaginal fluid or material during introduction or removal of the brush. The sheath preferably has an outside diameter of about 2 to 4 mm, more preferably about 2.8 mm, giving the brush an extremely small profile during introduction, smaller than many instruments used for the insertion of an intrauterine contraceptive device. This obviates the need for cervical dilation during use of the brush of the present invention and makes the brush especially useful for collecting samples from obese, diabetic, nulliparous or hypertensive postmenopausal women without significant discomfort to them. Moreover, because the sampling is atraumatic to the uterine canal, sampling can be carried out on a regular and routine basis (for example, for screening purposes), and does not cause injury or scarring which might otherwise interfere with another subsequent technique, as can occur with conventional full dilation and curettage. It should be pointed out, however, that the brush of the present invention is not intended as a substitute for dilation and curettage.

The uterine endometrial tissue sample brush of the present invention has significant advantages over prior devices. Most notably, the brush possesses good ability to exfoliate endometrial tissue without trauma to the uterine canal, and good ability to collect the exfoliated endometrial tissue, without sacrificing one ability for the other. This combination of exfoliating and collecting abilities is achieved even though the brush is easy to use and is non-invasive; is well tolerated by patients and does not require either general anesthesia or postprocedural treatment; is safe and cost effective; avoids contamination from endocervical and vaginal fluids and materials; obtains a sample representative of the entire endometrial cavity, one which is large enough to permit cytomorphologic studies even in asymptomatic patients for whom curettage is not indicated; avoids the excessive device manipulation and the traumatic scraping of the endometrial cavity encountered in the use of prior devices (the latter inevitably arises from conventional curettage and can be disturbingly severe); and provides samples whose interpretation is relatively easy to learn.

These advantages make the brush of the present invention useful in a wide variety of clinical applications, including the screening of patients at risk for endometrial carcinoma; the follow-up of patients receiving Tamoxifen or estrogen replacement therapy; the follow-up of patients with endometrial hyperplasia (either treated or untreated); the evaluation of postmenopausal women whose cervicovaginal smears show a high estrogen effect, prominent histiocytic activity and/or atypical endometrial cells; endometrial dating for patients with fertility disorders; and the procurement of uncontaminated endometrial samples (for microbiological cultures) in patients with endometritis. The uterine endometrial tissue sample brush of the present invention is also indicated for use in patients at high risk for endometrial adenocarcinoma (for example, those who are obese, diabetic, nulliparous, hypertensive or late-onset menopausal); for the follow-up of treated and untreated patients with endometrial lesions, for example, endometrial cancers or endometrial hyperplasia; and patients experiencing postmenopausal bleeding or other symptoms or signs warranting endometrial evaluation. Moreover, because the brush is atraumatic, its use does not interfere with the subsequent use of other evaluative techniques.

In a first aspect, then, the present invention is directed to a uterine endometrial tissue sample brush comprising a flexible core having a proximal core end and a distal core end, and a brush member carried adjacent the distal core end; wherein the brush member is about 3 to 5 cm long and has a free outside diameter suited to maintain patient comfort yet comprehensively contact the undilated uterine canal; and wherein the brush member comprises a plurality of resilient bristles axially spaced about 0.5 to 1.5 mm apart, each of the bristles having a stiffness equivalent to that possessed by nylon-6,12 at a diameter of about 0.076 to 0.152 mm; whereby the brush simultaneously possesses good ability to exfoliate endometrial tissue without trauma to the uterine canal and good ability to collect the exfoliated endometrial tissue on the brush member. This aspect of the present invention is also directed to a uterine endometrial tissue sample brush which includes any or all of the elements recited above, or identified in the detailed description of the invention recited below.

In a second aspect, the present invention is directed to a uterine endometrial tissue sample brush which comprises a specific combination of the elements recited above.

In a final aspect, the present invention is directed to a method for sampling uterine endometrial tissue, comprising the steps of providing a uterine endometrial tissue sample brush including a brush member as described, introducing the brush into the uterine canal, rotating and simultaneously moving the brush member distally in the uterine canal so as to exfoliate and collect endometrial tissue on the brush member, and withdrawing the brush from the uterine canal. This aspect of the present invention is also directed to certain steps specific to brushes incorporating certain of the elements recited above, or identified in the detailed description of the invention recited below.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
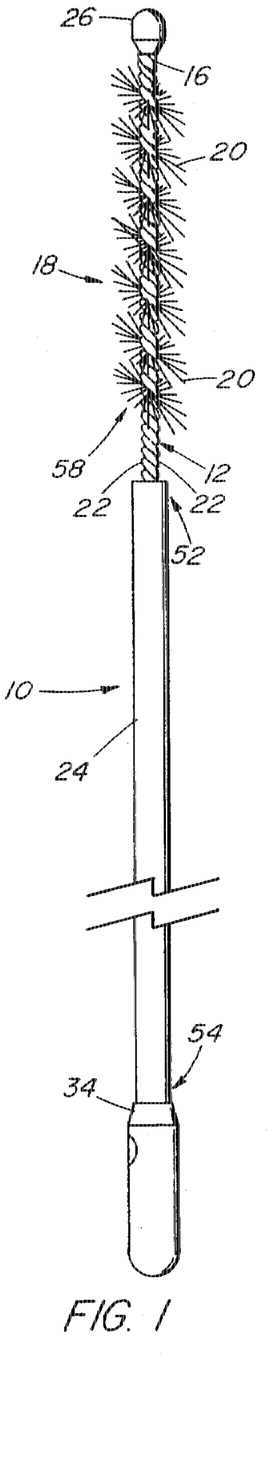
FIG. 1 is a perspective view of the preferred embodiment of the present invention.
Figure 2:
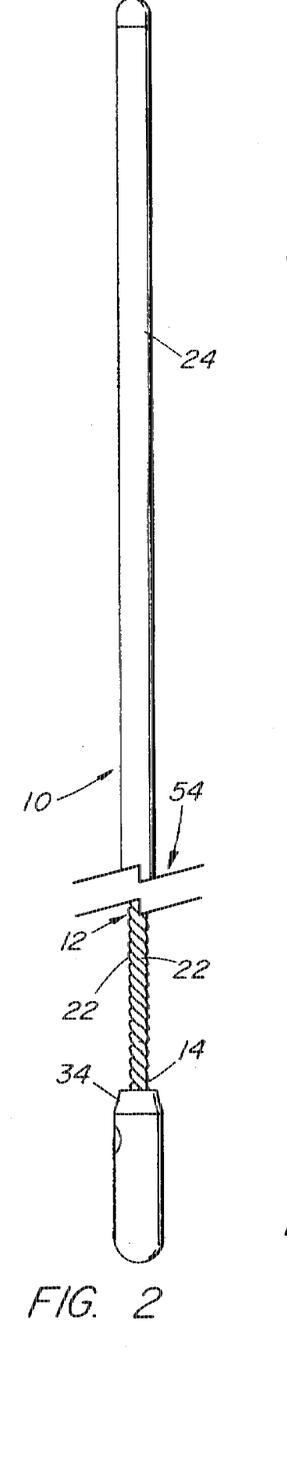
FIG. 2 is another perspective view of the preferred embodiment of the present invention.
Figure 3:
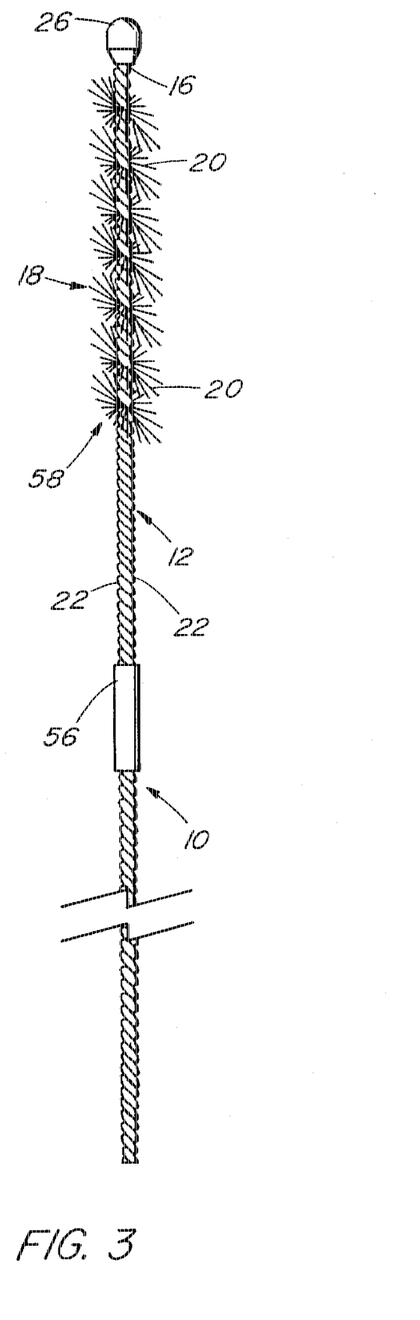
FIG. 3 is a partial perspective view of the preferred embodiment of the present invention, with a portion removed for clarity.

With reference first to FIGS. 1 through 3, the preferred embodiment of the present invention for sampling uterine endometrial tissue is thereshown as a brush 10 comprising a flexible core 12 having a proximal core end 14 and a distal core end 16, and a brush member 18 carried adjacent the distal core end 16. The core 12 is sufficiently flexible to render the brush 10 relatively comfortable during use, and prevent trauma to the uterus during insertion and removal. The core 12 can be composed of any suitable and sterilizeable medical grade material, such as a plastic, a polymer or the like. The core 12 cannot be so thin or so flexible as to be unable to pass into the uterus 36. Conveniently, the core 12 comprises a spirally wrapped pair of stainless steel wires 22, each having a diameter of about 0.508 mm (0.020 in.). The flexible core 12 is preferably about 18 cm long, and conveniently has a handle 34 proximally attached to its proximal end 14.

The brush member 18 is preferably about 3 to 5 cm long, more preferably about 3.5 cm long. While any of a variety of shapes may be useful, the brush member 18 is preferably uniformly cylindrical in shape, that is, the brush member 18 is preferably free of any taper of its diameter. The brush member 18 has a free outside diameter suited to maintain patient comfort yet comprehensively contact the undilated uterine canal. A free outside diameter of about 5.08 to 7.62 mm (0.2 to 0.3 in.) is preferred, and a free outside diameter of about 5.97 mm (0.235 in.) is more particularly preferred. In any event, however, the diameter of the brush member 18 should be as small as possible, so as to make use of the brush 10 comfortable for the patient, yet still be large enough to retrieve a proper tissue sample. A brush member 18 smaller than about 5.08 mm diameter may not adequately contact the uterine canal 38 during use, while a brush member 18 larger than about 7.62 mm diameter could be unacceptably uncomfortable during use to a significant number of patients.

The brush member 18 comprises a plurality of resilient bristles 20 axially spaced about 0.5 to 1.5 mm apart, and preferably axially spaced about 1 mm apart. The axial spacing of the bristles 20 can be individually or in groups, and conveniently the bristles are retained between the pair of wires 22 of the core 12, so that the bristles are continuously but spirally arrayed. The bristles 20 may instead be provided in discreet rows. The method of attaching the bristles 20 to the flexible core 12 is not believed to be critical to the successful practice of the present invention, and can be carried out in any conventional manner.

Each of the plurality of bristles 20 has a stiffness (flexural strength) equivalent to that possessed by nylon-6,12 at a diameter of about 0.076 to 0.152 mm (0.003 to 0.006 in.), preferably equivalent to that possessed at a diameter of about 0.127 mm (0.005 in.). This particular stiffness has been found critical to simultaneously giving the brush 10 good ability to exfoliate endometrial tissue without trauma to the uterine canal, and good ability to collect the exfoliated tissue on the brush member 18. A variety of synthetic, plastic and polymeric materials should be useful for the bristles 20, but most conveniently the bristles 20 are composed of nylon-6,12 and have the diameters indicated. It is important to remember that it is not the specific composition of the bristles 20 that is important to the success enjoyed by the present invention, but rather that the bristles 20 have a stiffness (and therefore an exfoliating and a collecting ability) equivalent to that recited.

The brush 10 also conveniently comprises a flexible sheath 24 disposed about the flexible core 12 and adapted to slidably receive the core 12 and brush member 18 therein. Alternatively, the sheath 24 can be viewed as being slidable along the flexible core 12. The sheath 24 can be composed of any suitable, sterilizeable medical grade material, such as a plastic, a polymer or the like. The specific composition of the sheath 24 is not deemed critical to the practice of the present invention. What is important, however, is that the sheath 24 does not diminish the flexibility of the brush 10; to the contrary, the flexibility of the sheath 24 should be selected to enhance placement of the brush 10 into various uterine configurations, such as retroverted or retroflexed. The sheath 24 is preferably about 16 cm long. The sheath 24 is dimensioned to compressively contain the brush member 18 therein when the sheath 24 is positioned over it. Conveniently, the sheath 24 has an outside diameter of no more than about 2.8 mm (0.110 in.). This makes the brush 10 particularly easy to introduce into the uterus 36.

The sliding of the sheath 24 relative to the core 12 and the brush member 18 is facilitated by a cylindrical guide 56 positioned over and affixed to the core 12. The guide 56 has an outside diameter about the same as, but slightly less than, the inside diameter of the sheath 24. The guide 56 can be composed of a suitable, sterilizeable medical grade metal, plastic or polymer, selected so that the sheath 24 slides over the guide 56. This sliding of the sheath 24 over the guide 56 can be relatively free, or can require the application of some small amount of force, so that the sheath 24 does not inadvertently change position during use. The guide 56 can be affixed to the flexible core 12 in any convenient manner, for example, by gluing, welding, soldering or the like. The guide 56 is conveniently positioned about 2 cm proximally of the proximal end 58 of the brush member 18.

Figure 4:
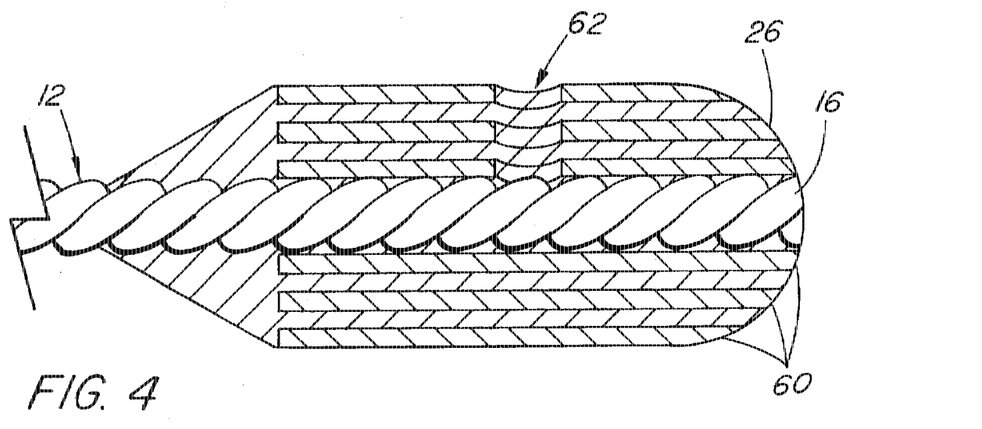
FIG. 4 is a cross-sectional view of a portion of the preferred embodiment of the present invention.

With continued reference to FIGS. 1 through 3, and with particular reference to FIG. 4, the flexible core 12 is rendered less traumatic during use by an atraumatic tip 26 included on the distal core end 16. The atraumatic tip 26 can be shaped in any suitable fashion, and its composition and construction is not believed critical to the success of the present invention. Conveniently, however, the atraumatic tip 26 is about 2.79 mm (0.110 in.) wide and about 2 to 3 mm long, sufficient to prevent the sheath 24 from sliding off the flexible core 12. Also conveniently, the tip 26 is constructed from several layers 60 of stainless steel or other suitable, sterilizeable medical grade tubing. The tubing layers 60 each include at least one perforation 62 through which solder (not shown) is introduced, in order to affix the tubing layers 60 to each other and to the distal core end 16. The atraumatic tip 26 is then ground to a smooth, rounded shape.

As indicated, it is the stiffness of the plurality of bristles 20 that is critical to the present invention. Their arrangement on the flexible core 12 can be adapted in a variety of ways.

Figure 5:
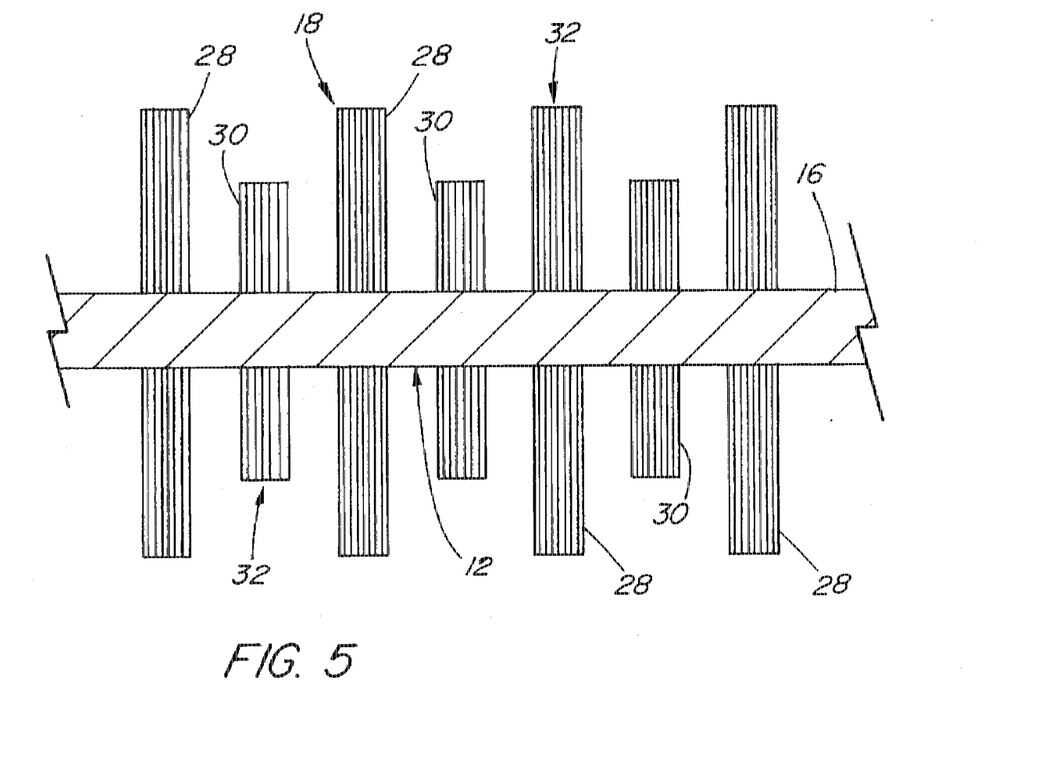
FIG. 5 is a cross-sectional, schematic view of a portion of another preferred embodiment of the present invention.

When present as discreet rows, the rows of bristles 20 can be of uniform stiffness, or as shown schematically in FIG. 5, alternating rows 28 and 30 of the bristles 20 can have lesser and greater stiffness, respectively. These differing stiffnesses give the rows 28 and 30 of bristles 20 differing exfoliating and collecting abilities. "Alternating" is used broadly in this regard, and does not mean strict alternation between one degree of stiffness and another, but merely that two or more different stiffnesses are provided to any two different, axially spaces rows 28 and 30 of the bristles 20.

The differing stiffnesses can be achieved in a variety of ways. For example, the bristles 20 of the rows 28 and 30 can have the same composition and diameter, but the bristles 20 of the less stiff row 28 longer (and more adapted for collecting) than the bristles 20 of the more stiff row 30 (and more adapted for exfoliating). Alternatively, the bristles 20 of the rows 28 and 30 can have the same composition and length, but the bristles 20 of the less stiff row 28 thinner than the bristles 20 of the more stiff row 30. The differing stiffnesses of the rows 28 and 30 can also be achieved by making their respective bristles from different materials. Moreover, the bristles of one of the rows 28 or 30 need not have a stiffness within the recited range, so long as the bristles 20 in the other of the rows 30 or 28 have a stiffness in the recited range. For example, a brush member 18 with some 0.0508 mm (0.002 in) diameter bristles and some 0.127 mm (0.005 in) diameter bristles would fall within the scope of the present invention, because the 0.127 mm bristles would constitute a plurality of bristles 20 falling within the recited range; the thinner bristles would be ancillary or optional. All of these variations are considered to be schematically illustrated by FIG. 5.

FIG. 5 also encompasses bristle rows 28 and 30 which are not discreet from one another. Such rows 28 and 30 of lesser and greater stiffness can be obtained even when they are formed from a single continuous array of bristles 20, for example, when the bristles 20 are retained between the pair of wires 22 and spirally arrayed. Offsetting the centers of the individual bristles 20 from the axis of the core 12, that is, from the axis about which the pair of wires 22 are spiralled, gives from a side view the same appearance of discreet rows 28 and 30 as in FIG. 5. A similar effect could be obtained by retaining groups of bristles 20 of differing lengths between more than two spirally wrapped wires 22.

Of course, any number of axially spaced rows 28 and 30 of bristles 20 having differing stiffnesses can be employed, as can rows of three or more different stiffnesses. In any case of axially spaced rows 28 and 30 of bristles 20 of differing stiffnesses, however, it is preferred that the average stiffness of all of the bristles 20 fall in the range of stiffness indicated above, and particularly preferred that the stiffnesses of all of the individual bristles 20 fall in that range.

As further schematically illustrated in FIG. 5, the individual bristles 20 conveniently include perpendicular end surfaces 32, without regard to the particular array or configuration in which the bristles 20 are disposed. The sharpness of the edges of the end surfaces 32 may improve the exfoliating ability of the bristles 20, and thus of the brush member 18. The end surfaces 32 are most easily obtained by cutting the bristles 20 to size after their attachment to the flexible core 12.

It must again be emphasized that, as used herein, "alternating" need not mean strict alternation between bristles 20 or rows of bristles 28 and 30 of only two different stiffnesses, that is, exfoliating and collecting abilities. The present invention also contemplates the presence of additional bristles or rows of bristles beside or between the axially spaced bristles 20, whether or not those additional bristles possess the equivalent stiffness defined above. Indeed, the present invention does not require that the axially spaced bristles 20 (nor the bristles 20 of the alternating rows 28 and 30) be longitudinally aligned. To the contrary, other arrangements of the bristles 20 on the brush member 18 may be highly advantageous.

Figure 7:
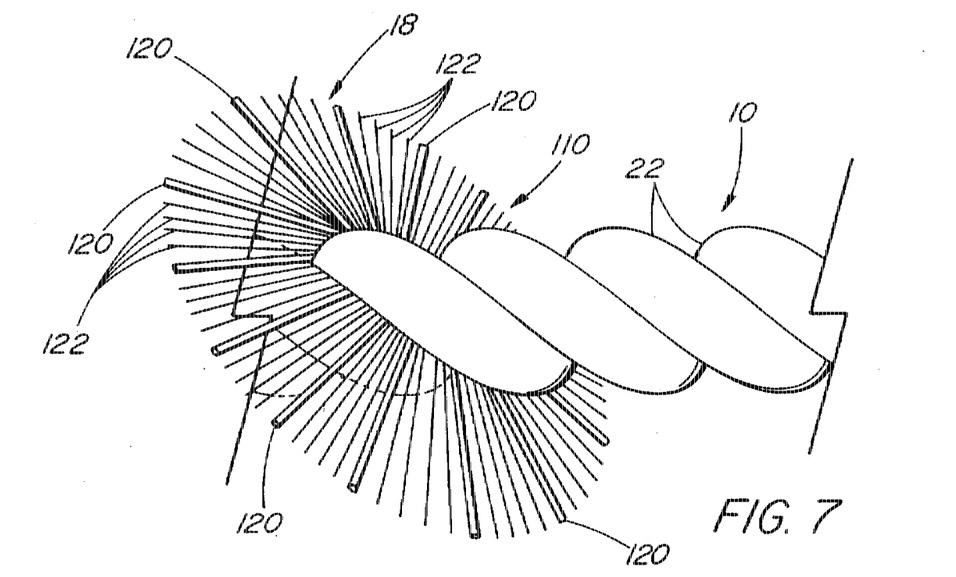
FIG. 7 is a side view of a portion of another preferred embodiment of the present invention.
Figure 8:
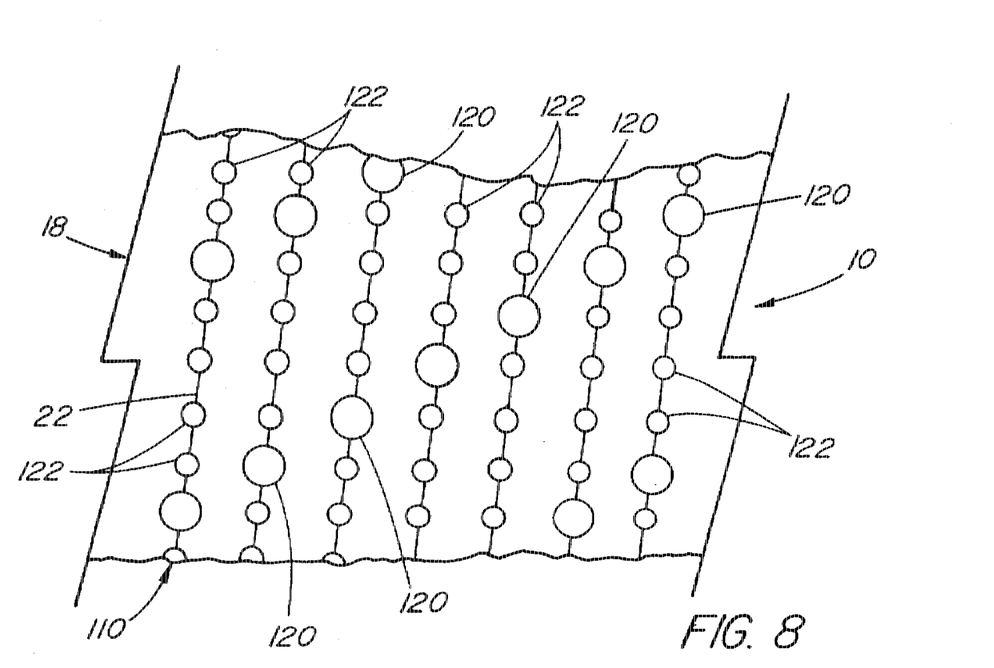
FIG. 8 is a schematic plan view of a portion of the surface of the embodiment shown in FIG. 7.

With reference to FIGS. 7 and 8, a particularly preferred and perhaps the most preferred embodiment of the present invention is thereshown, as a brush 10 like that disclosed in FIGS. 1 through 3, but in which bristles 20 having differing stiffnesses (and therefore differing exfoliating and collecting abilities) are regularly alternated while trapped and retained between the pair of wire 22 of the flexible core 12. More particularly, the bristles 20 comprise a series 110 of first bristles 120 possessing a first stiffness (specifically, the equivalent stiffness defined above), and a repeating plurality of second bristles 122 between each of the first bristles 120. For clarity, only half of a single helical row of the series 110 is shown in perspective in FIG. 7. The surface view of FIG. 8 discloses the way in which the first bristles 120 and second bristles 122 are arranged when retained between the pair of wires 22.

The second bristles 122 possess a second stiffness which can be either the same as or different from the first stiffness of the first bristles 120. Moreover, the second stiffness need not fall within the range given for the equivalent stiffness defined above; the resulting brush 10 will still possess axially spaced first bristles 120 having the requisite stiffness, even though they can be somewhat circumferentially offset. Thus, in the particularly preferred embodiment of FIGS. 7 and 8, the first bristles 120 have a diameter of 0.005 in. (0.127 mm), while the second bristles 122 have a diameter of 0.0025 in. (0.064 mm).

Any convenient number of second bristles 122 can be provided. For the diameters given above, it is particularly preferred that a plurality of four of the second bristles 122 be provided between each of the first bristles 120. The present invention of course contemplates larger and smaller pluralities of second bristles 122.

It should be noted that current brush manufacturing technologies will in practice likely result in a brush 10 whose bristles 20 are not as precisely aligned with respect to one another, in comparison to the depiction in FIG. 8.

Figure 6A:
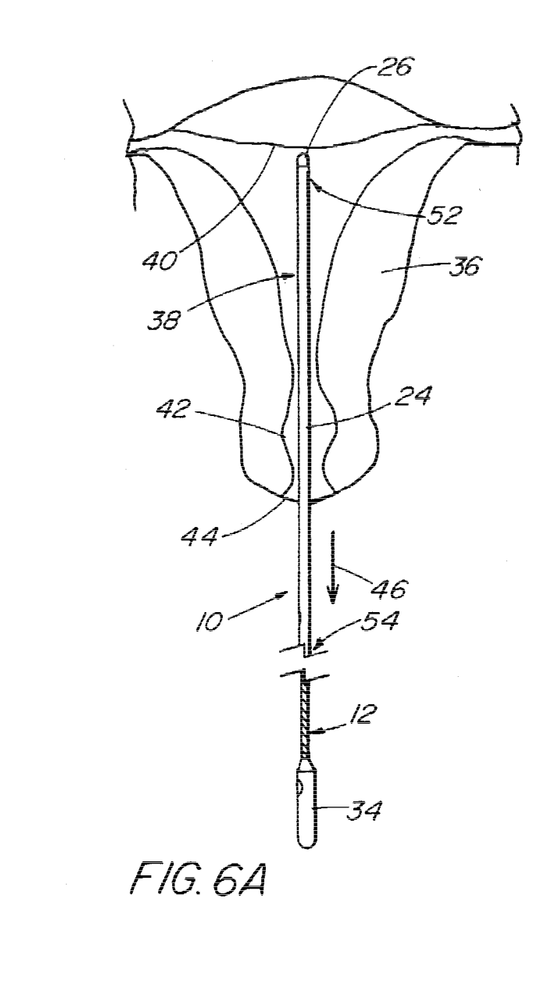
FIGS. 6A through 6C are perspective views of the preferred embodiment of the present invention during use, with the environment of use shown in cross-section.
Figure 6B:
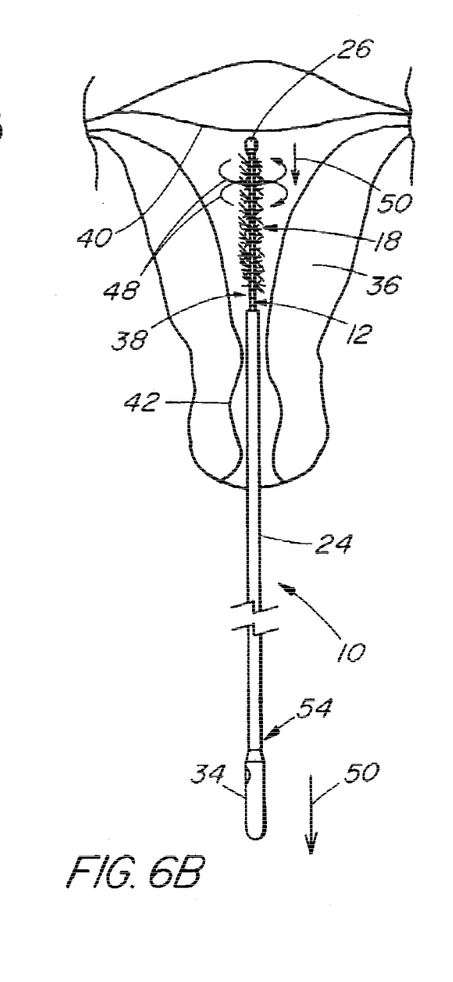
Figure 6C:
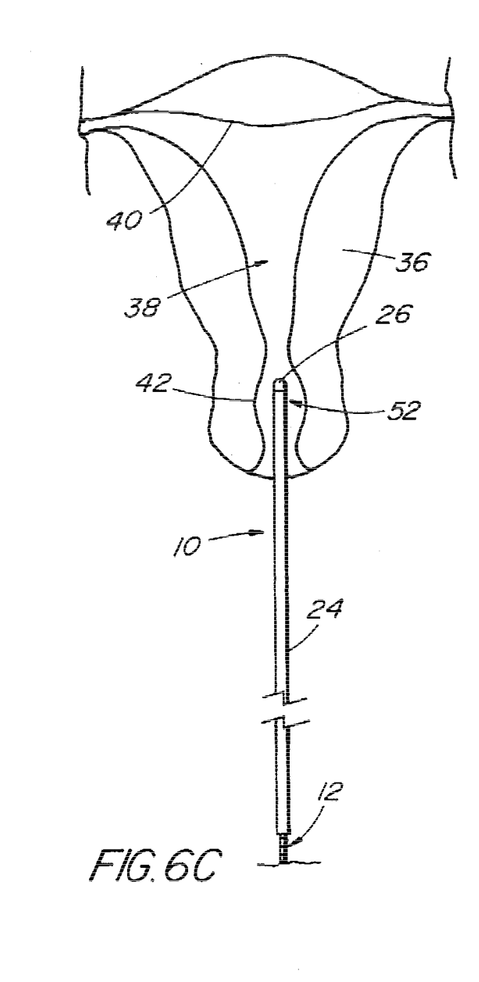

With reference now to FIGS. 6A through 6C, use of the brush 10 to sample uterine endometrial tissue can now be readily understood. It is preferred that the health practitioner intending to use the brush 10 of the present invention be familiar with conventional procedures for inserting intrauterine contraceptive devices, and such familiarity will be presumed for the purpose of the following explanation. It should be noted that the small diameter of the sheath 24 should make the insertion and use of the brush 10 even easier than the insertion of intrauterine contraceptive devices.

The sheath 24 is first positioned over the brush member 18 as shown in FIG. 2, with the distal end 52 of the sheath 24 abutting the atraumatic tip 26 on the flexible core 12. The brush member 18 is thereby compressively contained in the sheath 24. The patient is placed in the lithotomy position, and a sterile, non-lubricated vaginal speculum employed to render the external os 44 of the uterus 36 visible. If microbiological studies are planned, the ectocervix and the endocervical canal are then swabbed with povidone solution. The swab should be inserted about 1.5 cm into the endocervical canal to ensure adequate swabbing of the endocervix with the povidone. If microbiological studies are not planned, disinfection of the ectocervix and the endocervical canal is unnecessary.

The brush 10 then is gently inserted into the uterine canal 38, without changing the position of the sheath 24 over the brush member 18, until the atraumatic tip 26 reaches the level of the fundus 40 of the uterus 36 (the position shown in FIG. 6A). The sheath 24 prevents the brush member 18 from exfoliating and/or collecting any vaginal or exocervical fluids or materials during introduction of the brush 10, thereby assuring that such fluids or materials will not cause erroneous determinations of the condition of the uterine endometrial tissue.

Next, the sheath 24 is pulled all of the way proximally (outwardly) in the direction of arrow 46 until the proximal end 54 of the sheath 24 abuts the handle 34, exposing the brush member 18 to the uterine endometrium defining the uterine canal 38. The positions of the brush member 18 and sheath 24 which result from such action are shown in FIG. 6B. The length of the sheath 24 is such that the distal end 52 of the sheath 24 is thereby located at the level of the internal os 42 of the uterus 36. It should be noted that the normal uterine canal 38 is in a collapsed state, and that the canal 38 is shown expanded in FIGS. 6A through 6C only for clarity. The brush member 18, when positioned as shown in FIG. 6B, will have direct contact with the uterine endometrial surface along the entire length of the brush member 18.

Using the handle 34, the brush member 18 is then rotated in both directions, as shown by the arrows 48, and simultaneously pulled in a proximal (outward) direction as shown by the arrows 50, without moving the sheath 24 with respect to the uterus 36. The resulting position of the brush 10 and the sheath 24 is shown in FIG. 6C. The brush member 18 has thus exfoliated and collected material from along the entire length of the uterine canal 38, but the sheath 24 again protects the collected uterine endometrial material from contamination by vaginal or exocervical fluids or materials.

When the brush member 18 is fully contained in the sheath 24, the brush 10 is withdrawn from the uterus 36 to complete the sampling procedure. If microbiological studies are planned, the atraumatic tip 26 of the core 12 is wiped with a 95% alcohol gauze. The material collected by the brush is then analyzed in any conventional fashion. For example, if a morphologic evaluation is indicated, the sheath 24 will be pulled back to expose the brush member 18, and the brush member 18 used to prepare a direct smear on a sterile glass slide, which should be spray-fixed immediately. Alternatively, for culture studies, the exfoliated material collected on the brush member 18 (or which has become deposited on the flexible core 12) can be retrieved by agitating the brush member 18 in a suitable medium such as sterile Stuarts Transport Medium for an appropriate time, for example, about 5 seconds. Permanent preservation of any material still attached to the brush member 18 can be performed by shaking the brush member 18 in a suitable cytologic preservative (such as 20 to 30 ml of cytospin solution) to retrieve material, or by cutting the flexible core 12 proximal to the brush member 18, and dropping or otherwise placing the brush member 18 (and the portion of the core 12 carrying it) in a container of an appropriate cytologic preservative.

It is important to note that the sample material retrieved by the brush 10 of the present invention can be used for both cytological and histological diagnosis. Histology is performed from the fragments of tissue yielded by the brush 10. Tissue fragment histology increases the diagnostic accuracy of the brushing procedure. Cytology, in contrast, allows the physician to make a clinical decision regarding the condition of the patient. The brush 10 of the present invention facilitates both of these because it retrieves cytological samples which are more adequate, and histological samples which are more accurate, than the samples obtained with the standard sampling products on the market today.

With particular regard to morphologic evaluation, the brush 10 provides uterine endometrial tissue samples very well suited for the recognition of abnormal cells associated with a variety of conditions or circumstances, including but not limited to: those associated with or consistent with benign atypia (non-hyperplastic), such as acute inflammation, chronic inflammation, granulomatous inflammation, squamous metaplasia and irradiation effects; those associated with or consistent with endometrial hyperplasia, either mild, moderate or severe; and those associated with or consistent with malignancy, such as adenocarcinoma, adenocanthoma, mixed adenosquamous carcinoma, leiomyosarcoma, stromal sarcoma or the like; as well as the recognition of other abnormal cells not specifically classified above.

The brush 10 of the present invention is also useful for endocervical canal sampling. The endocervical procedure is substantially the same as that disclosed above, except that the brush 10 is inserted only to the point where the atraumatic tip 26 of the flexible core 12 reaches the level of the internal uterine os 42. For brevity, the remaining details of the procedure will not be repeated.

A few caveats should be noted in regard to the use of the brush 10 of the present invention. For example, the brush 10 is contraindicated for patients with a history of Caesarean section. Moreover, it is possible that the brush 10 may not collect an adequate endometrial sample in patients with postmenopausal bleeding who are at known increased risk of endometrial carcinoma; for such patients, consideration should be given to the alternative of formal dilation of the cervix, endometrial curettage and exploration of the uterine cavity under general anesthesia. The brush 10 of the present invention, however, is otherwise useful for a variety of patients.

The present invention thus provides a uterine endometrial tissue sample brush 10 having significant advantages over prior devices. Most notably, the brush 10 possesses good ability to exfoliate endometrial tissue without trauma to the uterine canal 38, and good ability to collect the exfoliated endometrial tissue, without sacrificing one ability for the other. This combination of exfoliating and collecting abilities is achieved even though the brush 10 is easy to use and is non-invasive; is well tolerated by patients; is safe and cost effective; avoids contamination from endocervical and vaginal fluids and materials; obtains a sample representative of the entire endometrial cavity; avoids the excessive device manipulation and the traumatic scraping of the endometrial cavity encountered in the use of prior devices; and provides samples whose interpretation is relatively easy to learn. These advantages make the brush 10 of the present invention useful in a wide variety of clinical applications, especially the routine screening of patients at risk for endometrial carcinoma and the follow-up of patients receiving Tamoxifen or estrogen replacement therapy. Notably, because the brush 10 is atraumatic, its use does not interfere with the subsequent use of other evaluative techniques.

The other details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of even rudimentary skills in this area, in view of the present disclosure.

Industrial Applicability

The present invention is useful in the performance of uterine endometrial tissue sampling procedures, and therefore finds applicability in human medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A uterine endometrial tissue sample brush (10) comprising:

a flexible core (12) having a proximal core end (14) and a distal core end (16); and a brush member (18) carried adjacent the distal core end (16);

wherein the brush member (18) is about 3 to 5 cm long and has a free outside diameter suited to maintain patient comfort yet comprehensively contact the undilated uterine canal (38); and wherein the brush member (18) comprises a plurality of resilient bristles (20) axially spaced about 0.5 to 1.5 mm apart, each of the bristles (20) having a stiffness equivalent to that possessed by nylon-6,12 at a diameter of about 0.076 to 0.152 mm; whereby the brush (10) simultaneously possesses good ability to exfoliate endometrial tissue without trauma to the uterine canal and good ability to collect the exfoliated endometrial tissue on the brush member (18).

2. The brush (10) according to claim 1, wherein the core (12) comprises a spirally wrapped pair of wires (22), and wherein the bristles (20) are retained between the pair of wires (22) so that the bristles (20) are spirally arrayed.

3. The brush (10) according to claim 1, wherein alternating rows (28 and 30) of axially spaced bristles (20) have differing stiffnesses and thereby possess differing exfoliating and collecting abilities.

4. The brush (10) according to claim 3, wherein the alternating rows (28 and 30) of axially spaced bristles (20) have differing diameters, thereby giving them differing stiffnesses.

5. The brush (10) according to claim 3, wherein the alternating rows (28 and 30) of axially spaced bristles (20) have differing lengths, thereby giving them differing stiffnesses.

6. The brush (10) according to claim 3, wherein the center of each bristle (20) is offset from the axis of the core (12).

7. The brush (10) according to claim 1, further comprising a sheath (24) adapted to slidably receive the core (12) and brush member (18) therein.

8. The brush (10) according to claim 7, wherein the sheath (24) has an outside diameter of no more than about 2.8 mm.

9. The brush (10) according to claim 7, wherein the sheath (24) is adapted to compressively contain the brush member (18) therein.

10. The brush (10) according to claim 1, wherein the distal core end (16) includes an atraumatic tip (26).

11. The brush (10) according to claim 1, wherein the brush member (18) is about 3.5 cm long.

12. The brush (10) according to claim 1, wherein the bristles (20) have a stiffness equivalent to that possessed by nylon-6,12 of about 0.127 mm diameter.

13. The brush (10) according to claim 1, wherein the bristles (20) include perpendicular end surfaces (32).

14. The brush (10) according to claim 1, wherein the brush member (18) is cylindrical in shape.

15. The brush (10) according to claim 1, wherein the bristles (20) are composed of nylon-6,12 about 0.076 to 0.152 mm in diameter.

16. The brush (10) according to claim 15, wherein the bristles (20) are about 0.127 mm in diameter.

17. The brush (10) according to claim 1, wherein the free outside diameter of the brush member (18) is about 5.08 to 7.62 mm.

18. The brush (10) according to claim 17, wherein the free outside diameter of the brush member (18) is about 5.97 mm.

19. The brush (10) according to claim 2, wherein the bristles (20) retained between the pair of wires (22) comprise a series (110) of first bristles (120) possessing a first stiffness equivalent to that possessed by nylon-6,12 at a diameter of about 0.076 to 0.152 mm, and a plurality of second bristles (122) between each of the first bristles (120).

20. The brush (110) according to claim 19, wherein the second bristles (122) possess a second stiffness different from the first stiffness possessed by the first bristles (120).

21. A uterine endometrial tissue sample brush (10) comprising:

a flexible core (12) having a proximal core end (14) and a distal core end (16), the core (12) comprising a spirally wrapped pair of wires (22), and the distal core end (16) including an atraumatic tip (26);

a cylindrical brush member (18) carried adjacent the distal core end (16), the brush member (18) being about 3.5 cm long and having an outside diameter of about 5.97 mm; wherein the brush member (18) comprises a spiral array of resilient bristles (20) axially spaced about 1 mm apart, the bristles (20) being retained between the spirally wrapped pair of wires (22), and the bristles (20) comprising a series (110) of first bristles (120) possessing a first stiffness equivalent to that possessed by nylon-6,12 at a diameter of about 0.076 to 0.152 mm, and a plurality of second bristles (122) between each of the first bristles (120), the second stiffness being different from the first stiffness; and a sheath (24) having an outside diameter of about 2.8 mm, adapted to slidably receive the core (12) and brush member (18) therein and to compressively contain the brush member (18) therein;

whereby the brush (10) simultaneously possesses good ability to exfoliate endometrial tissue without trauma to the uterine canal and good ability to collect the exfoliated endometrial tissue on the brush member (18).

22. A method for sampling uterine endometrial tissue, comprising the steps of:

providing a uterine endometrial tissue sample brush (10) comprising a flexible core (12) having a proximal core end (14) and a distal core end (16), and a brush member (18) carried adjacent the distal core end (16); wherein the brush member (18) is about 3 to 5 cm long and has a free outside diameter suited to maintain patient comfort yet comprehensively contact the undilated uterine canal (38); and wherein the brush member (18) comprises a plurality of resilient bristles (20) axially spaced about 0.5 to 1.5 mm apart, each of the bristles (20) having a stiffness equivalent to that possessed by nylon-6,12 at a diameter of about 0.076 to 0.152 mm; whereby the brush (10) simultaneously possesses good ability to exfoliate endometrial tissue without trauma to the uterine canal (38) and good ability to collect the exfoliated endometrial tissue on the brush member (18);

introducing the brush (10) into the uterine canal (38);

rotating and simultaneously moving the brush member (18) distally in the uterine canal (38) so as to exfoliate endometrial tissue from the uterine canal (38) and collect the exfoliated endometrial tissue on the brush member (18); and withdrawing the brush (10) from the uterine canal (38).

23. The method according to claim 22, wherein the providing step is carried out with a brush (10) further comprising a sheath (24) adapted to slidably receive the core (12) and brush member (18) therein; and wherein the method comprises the additional steps of:

sliding the brush member (18) into the sheath (24) before introducing the brush (10) into the uterine canal (38);

partially withdrawing the sheath (24) after introducing the brush (10) into the uterine canal (38) and before rotating and moving the brush member (18) in the uterine canal (38), so as to free the brush member (18) from the sheath (24); and holding the sheath (24) stationary while the brush member (18) is rotated and moved in the uterine canal (38), until the brush member (18) is received in the sheath (24).

24. The method according to claim 23, wherein the steps of the method are carried out with a brush (10) in which the sheath (24) has an outside diameter of no more than about 2.8 mm.

25. The method according to claim 22, wherein the steps of the method are carried out with a brush (10) in which alternating rows (28 and 30) of axially spaced bristles (20) have differing stiffnesses and thereby possess differing exfoliating and collecting abilities.

26. The method according to claim 22, wherein the steps of the method are carried out with a brush (10) in which the core (12) comprises a spirally wrapped pair of wires (22), in which the brush member (18) comprises a spiral array of the resilient bristles (20) retained between the pair of wires (22), and in which the bristles (20) retained between the pair of wires (22) comprise a series (110) of first bristles (120) possessing a first stiffness equivalent to that possessed by nylon-6,12 at a diameter of about 0.076 to 0.152 mm, and a plurality of second bristles (122) between each of the first bristles (120).

27. A uterine endometrial tissue sample brush (10) comprising:

a flexible core (12) having a proximal core end (14) and a distal core end (16), the core (12) comprising a spirally wrapped pair of wires (22), and the distal core end (16) including an atraumatic tip (26);

a cylindrical brush member (18) carried adjacent the distal core end (16), the brush member (18) being about 3.5 cm long and having an outside diameter of about 5.97 mm; wherein the brush member (18) comprises a spiral array of resilient bristles (20) axially spaced about 1 mm apart, the bristles (20) being composed of nylon-6,12 of about 0.127 mm diameter and being retained between the spirally wrapped pair of wires (22); and a sheath (24) having an outside diameter of about 2.8 mm, adapted to slidably receive the core (12) and brush member (18) therein and to compressively contain the brush member (18) therein;

whereby the brush (10) simultaneously possesses good ability to exfoliate endometrial tissue without trauma to the uterine canal and good ability to collect the exfoliated endometrial tissue on the brush member (18).

* * * * *